United States Patent [19]

Varaine

[11] Patent Number: 5,118,291

[45] Date of Patent: Jun. 2, 1992

[54] INSTRUMENT FOR REMOVING DEPOSITS AND STAINS ON TEETH

[75] Inventor: Jean-Pierre Varaine, Compiegne, France

[73] Assignee: Alain Triolet, Seraucourt Le Grand, France; a part interest

[21] Appl. No.: 678,708

[22] Filed: Apr. 1, 1991

[51] Int. Cl.⁵ .......................... A61C 3/06; A61C 3/00
[52] U.S. Cl. ........................... 433/142; 433/141; 433/147
[58] Field of Search ............... 433/141, 142, 146, 147

[56] References Cited

U.S. PATENT DOCUMENTS

| | | | |
|---|---|---|---|
| 737,616 | 9/1903 | Harrell | 433/147 |
| 1,105,457 | 7/1914 | Roberts | 433/142 |
| 3,660,902 | 5/1972 | Axelsson | 433/142 |
| 3,677,264 | 7/1972 | Brockman | 128/62 A |
| 3,775,848 | 12/1973 | Barnett | 132/89 |
| 3,862,065 | 1/1975 | Yokokawa et al. | 260/185 |
| 4,222,143 | 9/1980 | Tarrson et al. | 15/105 |
| 4,237,911 | 12/1980 | White | 132/89 |
| 4,435,160 | 3/1984 | Randklev | 433/9 |
| 4,780,083 | 10/1988 | Croll | 438/216 |
| 4,946,389 | 8/1990 | Weissenburger | 433/142 |

FOREIGN PATENT DOCUMENTS

| | | |
|---|---|---|
| 0001613 | 3/1979 | European Pat. Off. |
| 0001044 | 3/1979 | European Pat. Off. |
| 0158101 | 10/1985 | European Pat. Off. |
| 0168059 | 1/1986 | European Pat. Off. |
| 0337443 | 10/1989 | European Pat. Off. |
| 6442221 | 11/1987 | Japan ............... 433/142 |
| 6445577 | 11/1987 | Japan ............... 433/142 |

Primary Examiner—Cary E. O'Connor
Assistant Examiner—Cindy A. Cherichetti
Attorney, Agent, or Firm—Young & Thompson

[57] ABSTRACT

An instrument for removing deposits and stains on teeth is provided with a handle having an end-piece which carries a working tool, the tip of which is intended to be applied on the teeth to be treated. The tool consists of an eraser formed by a body of molded synthetic resin such as polyvinyl chloride, polyamide or silicone, within which are incorporated abrasive or polishing elements of greater hardness such that their Rockwell hardness number is higher than 25 mPa but lower than 200 mPa. These abrasive or polishing elements consist either of glass fibers with a fiber content on the order of 20 to 30% or of micrograins of a synthetic resin such as methyl polymethacrylate or a polyamide resin with a concentration within the range of 5 to 90% by weight, with a preference for a range of 20 to 50%, the particle diameter of these micrograins being approximately 10 to 400 microns. The eraser thus formed makes it possible to erase deposits and stains on teeth siimply by rubbing the eraser on the surface of the teeth.

11 Claims, 1 Drawing Sheet

1

INSTRUMENT FOR REMOVING DEPOSITS AND STAINS ON TEETH

BACKGROUND OF THE INVENTION

1. Field of the Invention

The present invention relates to instruments which are designed for cleaning teeth.

2. Description of the Prior Art

Apart from instruments used for professional purposes, namely those which are intended for dentists and which call for considerable dexterity as well as special precautions, instruments are already available to private individuals for cleaning certain parts of teeth. However, the instruments in question are designed for very specific operations such as scraping and the like. Thus U.S. Pat. No. 3,660,902 describes an instrument which is intended for this type of operation and consists of an operating handle having an elbowed end adapted to carry a working tool which can be engaged within the interstice between two teeth in order to clean this space. To this end, the tool body is of generally triangular shape having a decreasing surface so as to terminate in a relatively sharp point. Moreover, the lateral surfaces of the tool body have a series of raised rings surrounding depressions which are capable of retaining a polishing paste or the like. By reason of this very arrangement, a tool of this type can be employed only for cleaning the interstitial spaces between the teeth.

However, the most visible parts of the teeth are obviously their front faces which very frequently exhibit deposits and stains formed, for example, by products such as tobacco, coffee or tea or even certain drugs. The front faces of teeth are also very often coated with plaques of tartar or with a dental plaque. In order to remove these deposits and various stains, the services of a dentist are at present required in order to perform a cleaning operation by means of suitable professional instruments. For this reason, many persons refrain from undergoing such an operation as often as the need arises.

Accordingly, the object of the present invention is to provide a hand instrument which can be used with great ease by any unskilled person without any special precaution in order to remove deposits and stains which exist on the user's own teeth.

SUMMARY OF THE INVENTION

The invention is concerned with an instrument provided with an operating handle having an end-piece which carries a working tool, the tip of which is intended to be applied on the teeth to be treated. The distinctive feature of the instrument lies in the fact that the tool consists of an eraser formed by a body of molded synthetic resin such as polyvinyl chloride, polyamide or silicone, within which are incorporated polishing or abrasive elements having a higher value of hardness such that their Rockwell hardness number is higher than 25 mPa but lower than 200 mPa. These abrasive elements consist either of glass fibers with a fiber content on the order of 20 to 30% or of micrograins of a synthetic resin having an acceptable composition for teeth such as methyl polymethacrylate or a polyamide resin and having a concentration ratio within the range of 5 to 90% by weight, with a preference for a ratio of 20 to 50% and better still a ratio of 30 to 40%, the particle diameter of these micrograins being approximately 10 to 400 microns. The result thereby achieved is that the eraser thus formed makes it possible to erase deposits and stains on teeth simply by rubbing the eraser on the surface of the teeth.

In accordance with another distinctive feature of the instrument considered, the eraser carried by the end-piece of the operating handle is removably fixed on said end-piece by being partially engaged within a housing provided at the extremity of the end-piece, the opposite end of the handle being provided with a compartment containing at least a second similar eraser which is also adapted to be removably fixed within the housing formed at the extremity of the end-piece.

In an advantageous embodiment, a single operating handle is provided with a plurality of working erasers which are all adapted to be removably fixed within the housing formed at the extremity of the end-piece. these erasers being differentiated by the fact that they have work surfaces of different shapes such as a flat shape, a concave shape, and a pointed shape, a blade shape.

DETAILED DESCRIPTION OF THE INVENTION

Figure 1:
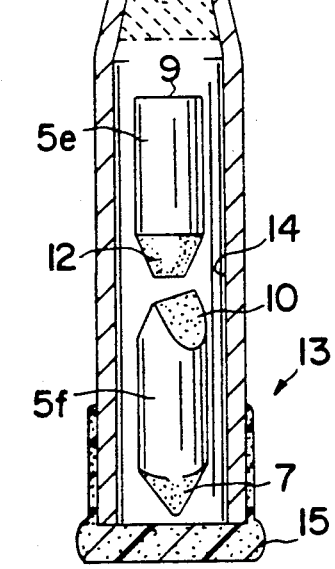
FIG. 1 is a view in elevation with portions broken away and showing an instrument in accordance with the invention.

As illustrated in FIG. 1, the instrument under consideration has an operating handle 1 which is intended to be held in one hand. One end of the handle is countercranked and terminates in a working end-piece 3 forming a housing 4 which has its opening at the extremity of the end-piece.

Said housing is intended to receive part of the body 5 of a working tool consisting of a kind of eraser, the particular characteristics of which are described hereinafter. In the example shown, the housing 4 provided in the end-piece 3 has a circular cross-section as is the case with the body of the handle 1. The body of the working tool 5 itself therefore has a circular cross-section such that the tool can be fitted with slight friction within the housing 4. If necessary, the tool body can carry an external rib 6 for limiting its engagement within the housing 4 so as to ensure that one of its two ends is located in an outwardly projecting position in order to constitute the working tool proper whilst the other end is placed within the housing 4 in such a manner as to ensure that the tool is perfectly held by the handle 1.

Figure 2:
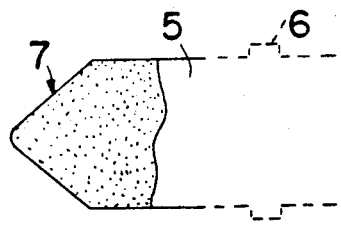
FIG. 2 is a partial view in elevation with portions broken away and showing a working tool fitted at the end of the operating handle of the instrument considered.

By virtue of this arrangement, the working eraser 5 is reversible since either end of the eraser can be placed in the outwardly projecting work position. The two ends of the eraser in fact constitute work surfaces having different shapes for potential applications which are also different. Thus, in the example illustrated in FIGS. 1 and 2, one end 7 of the eraser 5 is pointed whilst its opposite end 8 has a concave shape.

Figure 3:
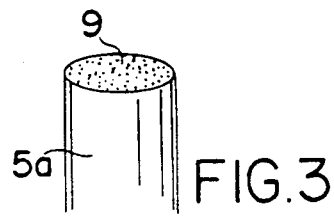
FIGS. 3 to 6 are views in perspective showing four different types of work surfaces of tools which can be fitted on the operating handle.
Figure 4:
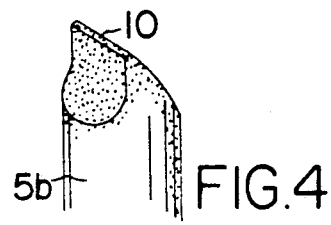
Figure 5:
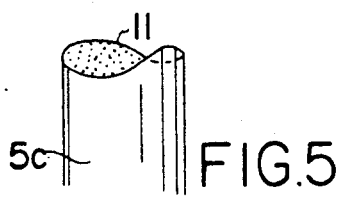
Figure 6:
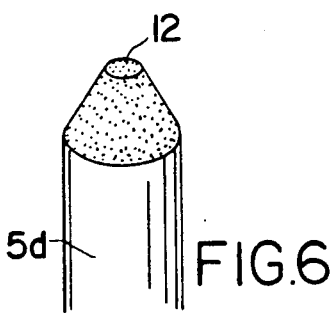

These shapes, however, are mentioned solely by way of example. In fact, with one and the same operating handle 1, provision is advantageously made for a series of reversible erasers which are similar to the eraser 5 and the ends of which have different shapes in order to constitute work surfaces which are also different. Moreover, FIGS. 3 to 6 illustrate different forms of work surfaces, for example:

- a flat end 9 in the case of the eraser 5a of FIG. 3;
- a blade-shaped end 10 in the case of the eraser 5b of FIG. 4;
- an end 11 of concave shape in the case of the eraser 5c of FIG. 5;
- a pointed end 12 having a flattened tip in the case of the eraser 5d of FIG. 6.

However, many other shapes of work surfaces may also be contemplated.

Preferably, the end portion 13 of the handle 1 which is opposite to the end-piece 3 has another housing 14 which is capable of serving as a storage compartment for two erasers 5e and 5f having work surfaces which are different from that of the eraser 5 which is fitted within the end-piece 3. Said eraser 5 can thus be replaced by either of the erasers 5e or 5f according to requirements. This compartment 14 is closed by an added end-cap 15 which can readily be removed.

The handle 1 can be manufactured by molding of injected plastic material. Preferably, the handle is hollow throughout its length and its end portion 13 is of greater width so that the reserve erasers can be placed freely within the corresponding compartment 14. In the example described, both this compartment and the housing 4 have a circular cross-section and the same applies to the working erasers. However, these different parts could just as well have a polygonal or oval cross-section or any other cross-section.

If so required, the eraser 5 which is placed in the work position can be fitted with a cap when the instrument in question is not in use with a view to satisfying the requisite conditions of hygiene.

Each working eraser is formed by a body of molded synthetic resin within which are incorporated polishing and/or abrasive elements having a higher degree of hardness. The resin constituting the eraser body can be polyvinyl chloride, a polyamide resin or else a silicone resin or any other suitable food-grade resin which is biocompatible with the different agents existing within the oral cavity. This resin must be chosen so as to ensure that the body thus formed has a very firm consistency while being elastically deformable to a slight extent. To this end, aside from the incorporated polishing and/or abrasion elements, the molded body of the eraser has a Shore A hardness number between 50 and 100, preferably between 60 and 100, or better still between 75 and 90.

The abrasive elements incorporated in the body of each eraser must have a Rockwell hardness number which is higher than 25 mPa while nevertheless remaining lower than 200 mPa. This maximum limit is chosen so as to take into account the fact that the Rockwell hardness of the dental enamel is 300 mPa, that the compressive strength of this enamel is 400 mPa and that the compressive strength of the ivory is 300 mPa.

In a first possible form of construction, the abrasive elements thus provided within the body of each eraser consist of glass fibers. In this case, provision is made for a fiber content on the order of 20 to 30% within the body of each eraser.

In another possible form of construction, the abrasive elements consist of micrograins of a synthetic resin having an acceptable composition for teeth, for example methyl polymethacrylate or a polyamide resin. The concentration ratio of these micrograins is within the range of 5 to 90% by weight with a preference for a ratio of 20 to 50% and better still 30 to 40%. The particle diameter of these micrograins is approximately 10 to 400 microns.

In both of these two forms of construction, the erasers thus produced are capable of removing stains and other deposits which exist on the surface of teeth, this being achieved by erasing simply under the action of rubbing of the work surface of this eraser against the tooth to be cleaned. In fact, the abrasive or polishing elements incorporated in these erasers are capable of removing stains and other deposits without any attendant danger of scoring or damaging the natural constituents of the teeth since the Rockwell hardness number of these elements is lower than that of the natural constituents of the teeth.

With the micrograins or glass fibers incorporated in the eraser body, it is possible to mix anti-tartar abrasive mineral elements such as carbonates, silicates, silica, and so on. It is also possible to incorporate in the body of each eraser anti-tartar products and/or products which are active against the formation of a dental plaque and/or antiseptic products, oral comfort agents, colorants, perfumes, fluorinated derivatives, composite resins, and so on.

By virtue of the fact that the working erasers are reversible and that provision is made for several erasers having different work surfaces, it is possible to select each time the working tool which is best suited to the shape of the tooth or portion of tooth to be cleaned.

The main advantage of the instrument in accordance with the invention lies in the fact that this instrument can be employed by any person without entailing the need to possess any particular dexterity or to take special precautions, which would not be the case with professional instruments used by dentists. In consequence, this instrument is primarily directed to the general public and enables anybody to clean the surface of his or her teeth without difficulty and without any need to resort to the services of a dentist. However, it is readily apparent that the instrument in accordance with the invention can also be used by professional practitioners in the field of odontostomatology as a scaling and polishing instrument.

If so required, this instrument can be employed by applying beforehand a polishing paste on the surface of the teeth. In such a case, the shape of the compartment 14 can be modified so that it may also contain a reserve supply of polishing paste or the like.

The work surfaces of the different erasers or of at least certain erasers can also be made more or less rough by forming grooves or small recesses or else raised or hollow patterns.

What is claimed is:

1. A hand instrument for the removal of deposits and stains on teeth, comprising an operating handle having an end-piece which carries a work tool, the tip of which is intended to be applied on the teeth to be treated, wherein said tool comprises an eraser formed by a body of molded synthetic resin selected from the group consisting of polyvinyl chloride, polyamide and silicone within which are incorporated abrasive elements having a higher value of hardness such that their Rockwell hardness number is higher than 25 mPa but lower than 200 mPa, these abrasive elements being composed of either glass fibers with a fiber content on the order of 20 to 30% or of micrograins of a synthetic resin having an acceptable composition for teeth selected from the group consisting of methyl polymethacrylate and polyamide resin and having a concentration ratio within the range of 5 to 90% by weight, the particle diameter of these micro-grains being approximately 10 to 400 microns, with the result that the eraser thus formed makes it possible to erase deposits and stains on teeth simply by rubbing the eraser on the surface of the teeth.

2. An instrument according to claim 1 wherein, aside from the incorporated abrasion elements, the molded body of the eraser has a Shore A hardness number between 50 and 100.

3. An instrument according to claim 2, wherein the molded body of the eraser has a Shore A hardness number between 60 and 100.

4. An instrument according to claim 3, wherein said Shore A hardness number is between 75 and 90.

5. An instrument according to claim 1, wherein the molded body of the eraser also contains anti-tartar abrasive mineral elements selected from the group consisting of carbonates and silicates.

6. An instrument according to claim 1, wherein the molded body of the eraser also contains at least one of anti-tartar products, anti-dental-plaque products, antiseptic products and composite resins.

7. An instrument according to claim 1, wherein the eraser carried by the end-piece of the operating handle is removably fixed on said end-piece by being partially engaged within a housing formed at the extremity of said end-piece, the opposite end portion of the operating handle being provided with a compartment containing at least a second similar eraser which is also adapted to be removably fixed within the housing formed at the extremity of the end-piece.

8. An instrument according to claim 7, wherein a single operating handle is provided with a plurality of working erasers which are all adapted to be removably fixed within the housing formed at the extremity of the end-piece, these erasers being differentiated by the fact that they have work surfaces of different shapes selected from a flat shape, a concave shape, a pointed shape and a blade shape.

9. An instrument according to claim 8, wherein each eraser has two distinct work surfaces having different shapes and formed at each end of the eraser body, each eraser being adapted to be removably fixed within the housing formed at the extremity of the end-piece by engagement of either end within said housing.

10. An instrument according to claim 1, wherein said micrograins of a synthetic resin have a concentration ratio within the range of 20 to 50% by weight.

11. An instrument according to claim 10, wherein said micrograins of a synthetic resin have a concentration ratio within the range of 30 to 40% by weight.

* * * * *